United States Patent
Belloni et al.

(10) Patent No.: US 6,194,175 B1
(45) Date of Patent: Feb. 27, 2001

(54) NUCLEIC ACIDS ENCODING TRUNCATED FORMS OF INHIBITORY KAPPA B PROTEIN

(75) Inventors: Paula Nanette Belloni, Half Moon Bay; Gary Allen Peltz, Redwood City, both of CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 09/349,627

(22) Filed: Jul. 8, 1999

Related U.S. Application Data

(62) Division of application No. 08/764,311, filed on Dec. 12, 1996, now abandoned.
(60) Provisional application No. 60/008,672, filed on Dec. 15, 1995, and provisional application No. 60/031,935, filed on Nov. 26, 1996.

(51) Int. Cl.[7] .......................... C12P 21/02; C12N 15/12; C12N 15/63
(52) U.S. Cl. ................. 435/69.1; 435/320.1; 536/23.5
(58) Field of Search ................. 536/23.1, 23.5; 435/320.1, 375, 69.1

(56) References Cited

U.S. PATENT DOCUMENTS

| | | |
|---|---|---|
| 4,675,189 | 6/1987 | Kent et al. . |
| 4,897,355 | 1/1990 | Eppstein et al. . |
| 5,364,791 | 11/1994 | Vegeto et al. . |

FOREIGN PATENT DOCUMENTS

| | | |
|---|---|---|
| WO 89/08147 | 9/1989 | (WO) . |
| WO 92/20795 | 11/1992 | (WO) . |
| WO 94/10305 | 5/1994 | (WO) . |
| WO 94/25608 | 11/1994 | (WO) . |

OTHER PUBLICATIONS

Brown et al., "Control of IκB–α Proteolysis by Site–Specific, Signal–Induced Phosphorylation", *Science* 267:1485–1488 (1995).

Scheinman et al., "Role of Transcriptional Activation of IκBα in Mediation of Immunosuppression by Glucocorticoids", *Science* 270:283–286 (1995).

Auphan et al., "Immunosuppression by Glucocorticoids: Inhibition of NF–κB Activity Through Induction of IκB Synthesis", *Science* 270:286–290 (1995).

Gossen et al., "Tight control of gene expression in mammalian cells by tetracycline–responsive promoters", *Proc. Natl. Acad. Sci. USA* 89:5547–5551 (1992).

W. French Anderson, "Prospects for Human Gene Therapy", *Science* 226:401–409 (1984).

Williams et al., "Retrovirus–mediated transfer of human adenosine deaminase gene sequences into cells in culture and into murine hematopoietic cells in vivo", *Proc. Natl. Acad. Sci. USA* 83:2566–2570 (1986).

Kinsella et al., "Episomal Vectors Rapidly and Stably Produce High–Titer Recombinant Retrovirus", *Hum. Gene Ther.* 7:1405–1413 (1996).

Sato et al., "Regulatory mechanism of 92 kDa type IV collagenase gene expression which is associated with invasiveness of tumor cells", *Oncogene* 8:395–405 (1993).

Baeuerle et al., "NF–κB: Ten Years After", *Cell* 87:13–20 (1996).

Nicolau et al., "In vivo expression of rat insulin after intravenous administration of the liposome entrapped gene for rat insulin I", *Proc. Natl. Acad. Sci. USA* 80:1068–1072 (1983).

Lin et al., "Expression of T Cell Antigen Receptor Heterodimers in a Lipid–Linked Form", *Science* 249:677–679 (1990).

Scherer et al., "Signal–induced degradation of IκBα requires site–specific ubiquitination", *Proc. Natl. Acad. Sci. USA* 92:11259–11263 (1995).

Rosenfeld et al., "Adenovirus–Mediated Transfer of a Recombinant α1–Antitrypsin Gene to the Lung Epithelium in Vivo", *Science* 252:431–434 (1991).

Mulligan et al., "Role of Endothelial–Leukocyte Adhesion Molecule 1 (ELAM–1) in Neutrophil–mediated Lung Injury in Rats", *J. Clin. Invest.* 88:1396–1406 (1991).

Imbert et al., "Tyrosine Phosphorylation of IκB–α Activates NF–κB without Proteolytic Degradation of IκB–α", *Cell* 86:787–798 (1996).

Logan et al., "Two enhancer regions in the mouse En–2 locus direct expression to the mid/hindbrain region and mandibular myoblasts", *Development* 117:905–916 (1993).

Sun et al., "Both Amino–and Carboxyl–Terminal Sequences within IκBα Regulate Its Inducible Degradation", *Mol. Cell. Biol.* 16:1058–1065 (1996).

Beg et al., "An Essential Role for NF–κB in Preventing TNF–α–Induced Cell Death", *Science* 274:782–784 (1996).

Wang et al., "TNF–and Cancer Therapy–Induced Apoptosis: Potentiation by Inhibition of NF–κB", *Science* 274:784–787 (1996).

Van Antwerp et al., "Suppression of TNF–α–Induced Apoptosis by NF–κB", *Science* 274:787–789 (1996).

*Primary Examiner*—Terry McKelvey
(74) *Attorney, Agent, or Firm*—Rohan Peries

(57) ABSTRACT

Truncated forms of inhibitory kappa B protein (IκB–α), nucleic acids encoding the truncates, expression and delivery vectors, and therapeutic and prophylatic uses thereof are provided.

10 Claims, 8 Drawing Sheets

Sequence of Human IκB N-terminal Truncation Mutant

```
ATGGTCAAGGAGCTGCAGGAGATCCGCCTCGAGCCCCAGGAGGTGCCGCGGGGCTCGGAGCCCTGGAAGCAG
 M  V  K  E  L  Q  E  I  R  L  E  P  Q  E  V  P  R  G  S  E  P  W  K  Q
CAGCTCACCGAGGACGGGGACTCGTTCCTGCACTTGGCCATCATCCATGAAGAAAAGGCACTGACCATGGAA
 Q  L  T  E  D  G  D  S  F  L  H  L  A  I  I  H  E  E  K  A  L  T  M  E
GTGATCCGCCAGGTGAAGGGAGACCTGGCCTTCCTCAACTTCCAGAACAACCTGCAGCAGACTCCACTCCAC
 V  I  R  Q  V  K  G  D  L  A  F  L  N  F  Q  N  N  L  Q  Q  T  P  L  H
TTGGCTGTGATCACCAACCAGCCAGAAATTGCTGAGGCACTTCTGGGAGCTGGCTGTGATCCTGAGCTCCGA
 L  A  V  I  T  N  Q  P  E  I  A  E  A  L  L  G  A  G  C  D  P  E  L  R
GACTTTCGAGGAAATACCCCCTGCACCTCCTGTGAGCAGGGCTGCCTGGCCAGCGTGGGAGTCCTGACT
 D  F  R  G  N  T  P  L  H  L  A  C  E  Q  G  C  L  A  S  V  G  V  L  T
CAGTCCTGCACCACCCCGCACCTCCACTCCATCCTTAAGGCTACCAACTACAATGGCCACACGTGTCTACAC
 Q  S  C  T  T  P  H  L  H  S  I  L  K  A  T  N  Y  N  G  H  T  C  L  H
TTAGCCTCTATCCATGGCTACCTCGGGATCGTGGAACTTTTGGTGTCCTTGGGTGCTGATGTCAATGCTCAG
 L  A  S  I  H  G  Y  L  G  I  V  E  L  L  V  S  L  G  A  D  V  N  A  Q
GAGCCCTGTAATGGCCGGACTGCCCTTCACCTGCAGGTGGACCTGCAAAATCCTGACCTGGTGTCACTCCTG
 E  P  C  N  G  R  T  A  L  H  L  A  V  D  L  Q  N  P  D  L  V  S  L  L
TTGAAGTGTGGGGCTGATGTCAACAGAGTTACCTACCAGGGCTATTCTCCTACCAGAAAACCTTCAGATGCTGCCAGAGAGTGAG
 L  K  C  G  A  D  V  N  R  V  T  Y  Q  G  Y  S  P  Y  Q  L  T  W  G  R
CCAAGCACCCGGATACAGCAGCTGGGCCAGCTGACACTCTAGAAAACCTTCAGATGCTGCCAGAGAGTGAG
 P  S  T  R  I  Q  Q  L  G  Q  L  T  L  E  N  L  Q  M  L  P  E  S  E
GATGAGGAGAGCTATGACACAGAGTCAGAGTTCACGGAGTTCACAGAGGACGAGCTGCCCTATGATGACTGT
 D  E  E  S  Y  D  T  E  S  E  F  T  E  F  T  E  D  E  L  P  Y  D  D  C
GTGTTTGGAGGCCAGCGTCTGACGTTA
 V  F  G  G  Q  R  L  T  L
```

Figure 1

NUCLEIC ACIDS ENCODING TRUNCATED FORMS OF INHIBITORY KAPPA B PROTEIN

CROSS REFERENCE TO RELATED APPLICATION

This application is a divisional of pending application Ser. No. 08/764,311, filed Dec. 12, 1996, now abandoned, and this application also claims the benefit under 35 U.S.C. 119(e) of U.S. Provisional Application No. 60/008,672, filed Dec. 15, 1995 and U.S. Provisional Application No. 60/031,935, filed Nov. 26, 1996. The entire disclosures of these prior applications are considered as being part of the disclosure of this divisional application and are hereby incorporated by reference.

BACKGROUND OF THE INVENTION a) Field of the Invention

The present invention relates to proteins which inhibit the activation of transcription factors, particularly of the transcription factor NFκB. The invention is also directed to the recombinant production of these proteins, particularly in vivo, and to methods for treating adult respiratory distress syndrome (ARDS), asthma, allograft rejection, vasculitis, and vascular restenosis, by means of genetic therapy, as well as other conditions that are typically responsive to inhibition of NFκB.

b) Description of Related Art

During inflammation, the expression of a number of different genes is up-regulated in epithelial and endothelial cells, including those coding for interleukins, transcription factors, adhesion molecules, and components of the coagulation system. Transcription of many of these genes involves the transcription factor NFκB.

The transcription factor NFκB is constitutively expressed in the cytoplasm of cells. Induction of gene transcription by NFκB-like proteins results from post-translational modification permitting translocation of the preformed transcription factor from the cytoplasm to the nucleus. This translocation is controlled by the phosphorylation and degradation of an inhibitor protein called IκB, which forms a complex with NFκB, and thereby holds it in the cytoplasm. Stimulation of the cell by appropriate signals leads to modification of IκB which in turn results in its dissociation from NFκB.

Binding of the IκB protein to NFκB masks the nuclear localization signal (NLS) of NFκB. Upon stimulation of the cell with specific agents, which depend on the cell type and stage of cell development, IκB is modified in a way that disables binding to NFκB, leading to dissociation of NFκB from IκB. Signals leading to this modification are believed to involve the generation of oxygen radicals, or kinase activation, and to lead to phosphorylation of IκB at specific sites; particularly at $^{32}$Ser, $^{36}$Ser, and $^{42}$Tyr. As a result its NLS is unmasked and NFκB is translocated to the nucleus, where it binds to specific DNA sequences in the regions which control gene expression. NFκB binding to these sites leads to transcription of genes involved in the inflammatory process.

The transcription factor NFκB was originally isolated from mature B cells where it binds to a decameric sequence motif in the κ light chain enhancer. Although NFκB was initially believed to be specific for this cell type and this stage of cell development, NFκB-like proteins have since been identified in a large number of cell types and, as discussed above, have been shown to be more generally involved in the induction of gene transcription. This has been further supported by the identification of functionally active NFκB binding sites in several inducible genes.

NFκB is a heterodimeric protein consisting of a 50 kD subunit (p50) and a 65 kD subunit (p65). The cDNAs for p50 and p65 have been cloned and have been shown to be homologous over a region of 300 amino acids. The p50 subunit shows significant homology to the products of the c-rel protooncogene isolated from mammals and birds, and to the Drosophila gene product of dorsal. Recently an additional member of the NFκB family, relB, has been cloned as an immediate early response gene from serum-stimulated fibroblasts.

Both p50 and p65 are capable of forming homodimers, although with different properties: whereas p50 homodimers have strong DNA binding affinity but cannot transactivate transcription, the p65 homodimers can only weakly bind to DNA but are capable of transactivation. p50 is synthesized as the amino-terminal part of the 110 kD precursor (p1110), which has no DNA binding and dimerisation activity. The carboxy-terminal part contains eight ankyrin repeats, a motif found in several proteins involved in cell cycle control and differentiation. Cloning of a shorter (2.6kb) RNA species which is induced in parallel with the 4 kb p50 precursor RNA has revealed that, either by alternative splicing or by differential promoter usage, the C-terminal part of the 110 kD protein can also be expressed independently.

Five Iκb family members have been identified: IκB-α, IκB-β, p105/IκB-γ, p100/IκB-Δ, and IκB-ε (Baeuerle and Baltimore, Cell 87:13–20, 1996). All IκB-like family members contain multiple ankyrin repeats, which are essential for inhibition of NF-κB activation.

The IκBα-like proteins contain five ankyrin repeats. RL/IF-1 has been cloned and shown to be expressed in regenerating liver within 30 minutes after hepatectomy. Deletion mutagenesis studies have revealed that four out of the five ankyrin repeats of pp40 are essential to inhibit DNA binding activity and to associate with c-rel, and that also the C-terminal region is required. Studies with monospecific antibodies, conducted with the 110 kD p50 precursor, have demonstrated that the C-terminal part (the part with IκB activity) masks the nuclear localization signal (NLS) located in the amino-terminal region of p50. Brown et al. in Science 267:1485–1488 (1995) reported an IκB deletion mutant, lacking 54 NH$_2$-terminal amino acids, which was neither proteolyzed nor phosphorylated by signals and continued to fully inhibit NFκB. Scheinman et al. and Auphan et al. have reported that glucocorticoid induced immunosuppression is mediated through induction of IκB synthesis (Science, 270:283–285 and 286–290 (1995)).

It is an object of this invention to provide IκB-like muteins which are not deactivated in vivo and thus continue to inhibit NFκB and impede or prevent the induction of inflammation.

SUMMARY OF THE INVENTION

This invention provides a biologically active protein, said protein mimicking the activity of IκB by inhibiting nuclear factor kappa B (NF-κB) mediated activation of the inflammatory response, said protein selected from the group consisting of the Δ(290–317), Δ(281–317), Δ(267–317), Δ(243–317), and Δ(1–44) truncates of IκB-α (SEQ ID NO:1).

A preferred aspect is the provision of cDNA encoding the truncated proteins. In a further aspect a cDNA encoding the Δ(1–44) IκB mutein is provided (SEQ ID NO: 2).

In another aspect, the invention relates to a method of treating respiratory disorders, particularly adult respiratory distress syndrome (ARDS), allograft rejection, asthma, inflammatory arthritis, vasculitis, cancer and restenosis in a mammal by administering to a mammal in need of such treatment a therapeutically effective amount of a protein selected from the group consisting of the Δ(290–317), Δ(281–317), Δ(267–317), Δ(243–317), and Δ(1–44) truncates of IκB-α (SEQ ID NO:1) via the in vivo or in vitro delivery of a nucleic acid encoding for a protein selected from the group consisting of the Δ(290–317), Δ(281–317), Δ(267–317), Δ(243–317), and Δ(1–44) truncates of IκB-α to a mammalian cell and the expression thereof in the cell to provide a therapeutically effective amount of the protein. In a preferred embodiment the nucleic acid is that encoding the Δ(1–44) truncate (SEQ ID NO:2).

BRIEF DESCRIPTION OF THE DRAWINGS

FIGS. 1a–1b. Sequence of IκB n-termninal Truncation mutant.

DETAILED DESCRIPTION OF THE INVENTION

Definitions and General Parameters

Figure 2:
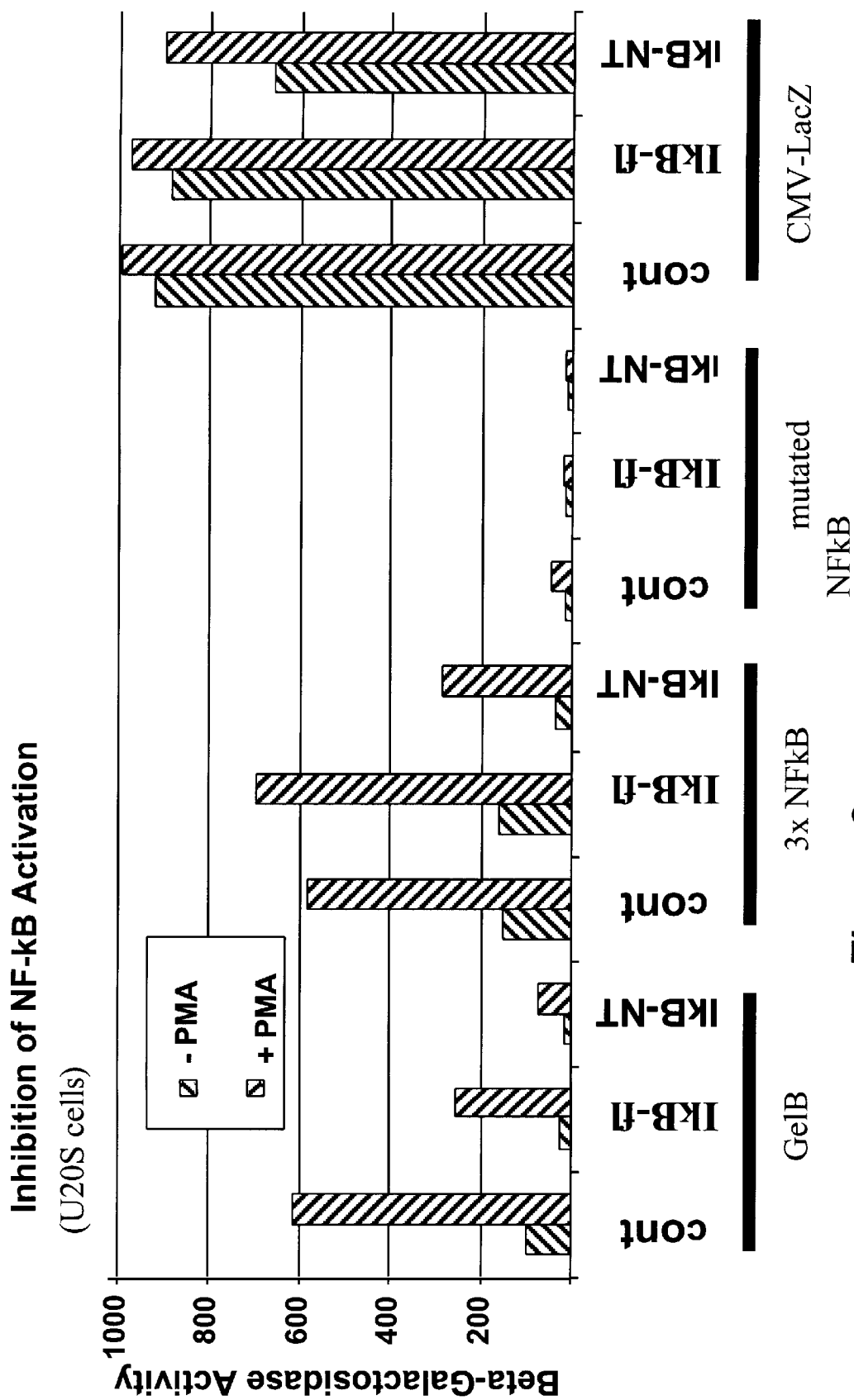
FIG. 2. IκB mutein inhibition of NF-κB activation in U2OS cells.

The following definitions are set forth to illustrate and define the meaning and scope of the various terms used to describe the invention herein.

The term "treatment" or "treating" means any treatment of a disease in a mammal, including: (i) preventing the disease, that is, causing the clinical symptoms of the disease not to develop; (ii) inhibiting the disease, that is, arresting the development of clinical symptoms; and/or (iii) relieving the disease, that is, causing the regression of clinical symptoms.

The term "effective amount" means a dosage sufficient to provide treatment for the disease state being treated. This will vary depending on the patient, the disease and the treatment being effected.

As used herein the terms "transformed" and "transfected" denote the introduction of a polynucleotide, e.g. cDNA, encoding an IκB mutein into a target cell.

"Operatively linked" refers to juxtaposition such that the normal function of the components can be performed. Thus, a coding sequence "operatively linked" to control sequences refers to a configuration wherein the coding sequence can be expressed under the control of these sequences.

"Control sequences" refers to DNA sequences necessary for the expression of an operatively linked coding sequence in a particular host organism. The control sequences which are suitable for eucaryotic cells are promoters, polyadenylation signals, and enhancers.

"Expression system" refers to DNA sequences containing a desired coding sequence and control sequences in operable linkage, so that cells transformed with these sequences are capable of producing the encoded proteins. In order to effect transformation, the expression system may be included on a vector; however, the relevant DNA may then also be integrated into the host chromosome.

"Vector" means a DNA molecule comprised of single strand, double strand, circular, or supercoiled DNA. The vector is comprised of the following elements operatively linked at appropriate distances for allowing functional gene expression: a promoter, a 5' mRNA leader sequence, a transcription initiation site, a nucleic acid cassette, a 3' untranslated region, and a polyadenylation site. One or more of these elements can be eliminated for specific applications. The nucleic acid cassette can include a restriction site for insertion of the nucleic acid sequence to be expressed. In a functional vector the nucleic acid cassette contains the nucleic acid sequence to be expressed including translation initiation and termination sites.

As used herein, the term "pharmaceutically acceptable" refers to a carrier medium which does not interfere with the effectiveness of the biological activity of the active ingredients and which is not toxic to the hosts to which it is administered.

The present invention concerns truncated forms of the inhibitory kappa B protein (IκB-α) selected from the group consisting of the Δ(290–317), Δ(281–317), Δ(267–317), Δ(243–317), and Δ(1–44) truncates of IκB-α (SEQ ID NO:1). A preferred embodiment is the N-terminal truncated form of the inhibitory kappa B protein (denoted IκB-NT) having the sequence Δ(1–44) (SEQ ID NO: 1). The truncated IκB proteins (IκBΔ290, IκBΔ281, IκBΔ267, IκBΔ243, and IκB-NT) resist proteolytic degradation, induced by inflammation, yet retains the ability to bind to NF-κB and to inhibit its transcriptional activity. These properties enable the recombinant truncated IκB protein to function as a potent inhibitor of NF-κB activation, indicating it will have significant anti-inflammatory activity. cDNA encoding IκB-NT may be expressed in pulmonary capillary endothelial cells to treat adult respiratory distress syndrome (ARDS), asthma, vasculitis, and inflammatory arthritis. In addition, transplanted organs or venous grafts may be treated with this formulation to inhibit allograft rejection. Vascular endothelium can be treated with a truncate via a catheter after PTCA to inhibit restenosis.

The IκB-NT truncation mutant (encoding amino acids 45–317) has several significant advantages over other IκB molecules and mutant IκB proteins as inhibitors of NF-κB activation. This truncation mutant lacks 44 NH$_2$-terminal amino acids of IκB-α, which regulate the signal-dependent degradation of this protein in response to a large variety of cellular activation signals. The serines at residue 32 and 36 are phosphorylated, lysines at positions 22 and 23 are ubiquitinated (Scherer et al., *PNAS* (USA) 92:11259–11263 (1995), and the tyrosine at position 42 (Imbert et al., *Cell* 86:787–798 (1996) is phosphorylated in response to activating signals. These events lead to the separation of IκB-α from NF-κB, resulting in NF-κB activation and degradation of IκB-α. Therefore, deletion of all three critical signalling sites on the IκB-NT truncation mutant produces an NF-κB inhibitor which resists activation dependent proteolytic degradation. In addition, the truncation mutant will be less immunogenic when expressed as a gene therapy than an IκB-α mutant which contains amino acid substitutions. In addition, IκB-β must be phosphorylated before it is able to inhibit NF-κB activation, while unphosphorylated IκB-α can inhibit NF-κB.

The IκB muteins described herein consist of proteinaceous material having a defined chemical structure. However, the precise structure depends on a number of factors, particularly chemical modifications known to occur to proteins. For example, since all proteins contain ionizable amino and carboxyl groups it is, of course, apparent that the inhibitor may be obtained in acidic or basic salt form, or in neutral form. It is further apparent, that the primary amino acid sequence may be augmented by derivatization using sugar molecules (glycosylation) or by other chemical derivatizations involving covalent, or ionic attachment to the inhibitor with, for example, lipids, phosphate, acetyl groups and the like, often occurring through association with saccharides. These modifications may occur in vitro, or in vivo, the latter being performed by a host cell through post-translational processing systems. It will be understood that such modifications, regardless of how they occur, are intended to come within the definition of IκB mutein so long as its activity is not destroyed. It is to be expected, of course, that such modifications may increase or decrease the biological activity of the molecule, and such chemically modified molecules are also intended to come within the scope of the invention.

The cDNA encoding human full length IκB (amino acids 1–317) was isolated from a cDNA library prepared from human umbilical vein endothelial cell (HUVEC) mRNA by PCR amplification using standard methodology. This cDNA was ligated into a eukaryotic expression plasmid (pBjneo) after digestion with restriction endonucleases EcoRI and XbaI to produce the plasmid pIκB-fl. The IκB truncation mutants (encoding amino acids 1–289, 1–280, 1–266, 1–242, and 45–317) were constructed by PCR amplification using the plasmid encoding full length human IκB as template. The preferred deletion mutant (IκB-NT) lacks at least the first 44 amino-terminal amino acids; it is expected that N-terminal deletion mutants up to des-Ser$^{70}$, start of the first ankyrin repeat, will also be effective.

Alternative methods of cloning, amplification, expression, and purification will be apparent to the skilled artisan. Representative methods are disclosed in Sambrook, Fritsch, and Maniatis, *Molecular Cloning, a Laboratory Manual*, 2nd Ed., Cold Spring Harbor Laboratory (1989).

Utility and Administration

The expression products, i.e. the IκB muteins, of this invention are useful for the prevention and treatment of a variety of mammalian conditions in which anti-inflammatories are indicated. In particular, the muteins of this invention are indicated for the prophylaxis and therapeutic treatment of adult respiratory distress syndrome (ARDS), allograft rejection, asthma, inflammatory arthritis, vasculitis, and vascular restenosis in humans.

The muteins of this invention are also useful in the treatment of diseases where inhibition of NF-κB produces a desirable therapeutic effect. For example, repression of NF-κB has been shown to promote programmed cell death or apoptosis, in particular apoptosis mediated by tumor necrosis factor, thus allowing apoptosis to be stimulated by the treatment with NF-κB repressors such as the IκB muteins described herein. It has also been shown that many conventional anticancer therapies result in activation of NF-κB which subsequently prevents tumor cell apoptosis and that resistance to anticancer therapies is due in part to resistance to apoptosis (Amer A. Beg and David Baltimore, *Science*, 274, 782–784 (1996); Cun-Yu Wang, Marty W. Mayo and Albert S. Baldwin, *Science*, 274, 784–787 (1996) and Inder M. Verma et al. *Science*, 274, 787–789 (1996)). Therefore, the IκB muteins described herein can be used to treat cancers, such as for example, breast cancer, by enhancing apoptosis of tumor cells by co-treatment with tumor necrosis factor, radiation or chemotherapeutic drugs such as daunorubicin, vincristine and etoposide. Additionally, combination treatment with TNF can be used to treat conditions in which certain cells need to be cleared, such as in bacterial and viral infections.

The muteins of this invention are also useful in the generation of antibodies to IκB and their subsequent use as diagnostics and pharmaceutical screening tools. The expression vectors are useful in generating NF-κB suppressed mammalian cells for evaluation of the immune response.

A further aspect of the present invention relates to pharmaceutical compositions comprising as an active ingredient a protein of the present invention, or pharmaceutically acceptable salt thereof, in admixture with a pharmaceutically acceptable, non-toxic carrier. Such compositions may be prepared for parenteral (subcutaneous, intramuscular or intravenous) administration, particularly in the form of liquid solutions or suspensions; for oral or buccal administration, particularly in the form of tablets or capsules; for pulmonary or intranasal administration, particularly in the form of powders, nasal drops or aerosols; and for rectal or transdermal administration.

The compositions may conveniently be administered in unit dosage form and may be prepared by any of the methods well-known in the pharmaceutical art, for example as described in *Remington's Pharmaceutical Sciences*, 17th ed., Mack Publishing Company, Easton, Pa., (1985).

Delivery of the compounds of the present invention to the subject over prolonged periods of time, for example, for periods of one week to one year, may be accomplished by a single administration of a controlled release system containing sufficient active ingredient for the desired release period. Various controlled release systems, such as monolithic or reservoir-type microcapsules, depot implants, osmotic pumps, vesicles, micelles, liposomes, transdermal patches, iontophoretic devices and alternative injectable dosage forms may be utilized for this purpose. Localization at the site to which delivery of the active ingredient is desired is an additional feature of some controlled release devices, which may prove beneficial in the treatment of certain disorders.

One form of controlled release formulation contains the protein or its salt dispersed or encapsulated in a slowly degrading, non-toxic, non-antigenic polymer such as copoly (lactic/glycolic) acid, as described in the pioneering work of Kent, Lewis, Sanders, and Tice, U.S. Pat. No. 4,675,189. The compounds or, preferably, their relatively insoluble salts, may also be formulated in cholesterol or other lipid matrix pellets, or silastomer matrix implants. Additional slow release, depot implant or injectable formulations will be apparent to the skilled artisan. See, for example, *Sustained and Controlled Release Drug Delivery Systems*, J. R. Robinson ed., Marcel Dekker, Inc., New York, 1978, and R. W. Baker, *Controlled Release of Biologically Active Agents*, John Wiley & Sons, New York, 1987.

Although it may be possible to deliver an effective amount of mutein itself to the target tissue, the problems of proteolytic degradation and low delivery efficiency make it most desirable to express a mutein of this invention in situ, preferably in the cytoplasm, whereby NFκB mediated transcription activation may be inhibited by preventing migration of NFκB into the nucleus.

In one embodiment this invention provides a heterologous cDNA sequence which is constitutively expressed in target cells and encodes an IκB mutein as described herein. The IκB mutein encoding sequence is operably linked with a heterologous promoter sequence, such that the mutein is expressed continuously. Typical promoters include, but are not limited to, CMV, SV40, and heat shock promoters.

In another embodiment a cDNA sequence encoding a mutein of this invention is operably linked with a heterologous inducible promoter sequence, so that expression is triggered by specific exogenous stimuli. A suitable exogenous stimuli may be provided either by the natural progression of the complement cascade or via the introduction of a foreign drug into the targeted cell or via some other non-chemical, external stimuli, such as irradiation. Representative inducible promoter systems are the steroid "gene switch" technology described in U.S. Pat. No. 5,364,791 (Vegeto et al.), and the tetracycline sensitive system reported by Gossen et al. in PNAS 89:5547–5551 (1992).

It is contemplated that this invention may be practiced either in vivo or ex vivo as appropriate for the condition being treated, the therapeutic regimen employed, and the overall health of the patient. Depending upon the selected protocol, a variety of techniques are useful for the introduction of the cDNA into the target cells. Many of the techniques are equally useful in either in vivo or ex vivo transfection; however, the skilled artisan will appreciate that certain techniques are more appropriate in a given situation and be guided accordingly. In general, the techniques may be divided into physical, chemical, and biological categories, as discussed more fully below.

Among the biological transfection techniques are included the use of retroviruses, adenoviruses, adeno-associated viruses, pox viruses, and bacterial plasmids.

Retroviral vectors are derived from retroviruses that replicate by randomly integrating their genome into that of the host. Retroviral vectors can carry a larger genetic payload than other viral vectors. However, retroviral vectors have inherent safety issues including contaminating viruses or retroviral genes already present in a patient which may produce viral products. They can enable the retroviral vector to regain its replicating potential and become a fully functional virus. Retroviral vectors are useful in muscle, brain, and other cells that do not proliferate. Suitable retroviral vectors are described in WO 92/07573.

The adenovirus is a linear, double-stranded DNA virus. While adenovirus serotypes are associated with respiratory infections, several non-infectious serotypes exist. Adenoviruses have an intermediate sized genome that replicates in the cell nucleus. Adenoviruses enter cells through receptors, and their viral DNA then migrates to the nucleus and is expressed. They have an affinity for respiratory epithelium and may be useful for therapy of lung and airway disorders. They also can be used to target epithelial cells. They make high titers, are relatively stable, and, because they are DNA viruses, can be delivered with an aerosol. These viruses are relatively easy to work with and because, they do not enter the chromosome, concerns about insertional mutagenesis are alleviated. There are some limitations to the use and development of adenoviral vectors. Since the genome of adenoviruses is linear, they are less stable and more prone to transcriptional errors. The cell lines used to produce the adenoviral vectors yield only low levels of infectious viral vectors and there is a persistence of native, wild-type virus. Further, antibodies to adenoviruses may act against these transformed adenoviruses. Suitable adenoviral vectors are described in Rosenfeld, et al., Science, 252:432 (1991).

Adeno-associated viruses (AAV) belong to the parvovirus family and consist of a single strand of DNA of about 4 to 6 kb. AAV vectors are stable in host cells, and there is no evidence that AAV alters cell gene expression or causes genetic rearrangement. AAV is limited by the minimal amount of genetic material that can be carried. Only about 5 kb of DNA can be packaged into an AAV vector.

Poxviral vectors are large viruses and have several sites in which genes can be inserted. They are thermostable and can be stored at room temperature. Safety studies indicate that poxviral vectors are replication defective and cannot be transmitted from host to host or to the environment. As with other viruses, there are inherent safety issues of recombination and formation of infectious particles. The pox virus is taken up by phagocytosis and therefore will enter a heterologous population of cells.

Plasmids are double-strands of DNA found in bacteria that replicate, transcribe, and translate independently of the bacterial genome. Plasmids from bacteria have been found to be adequate vectors for gene delivery. Replication genes may be removed from the plasmid to prevent it from being passed on to progeny cells. For example, when injected into muscle tissue, the plasmid is taken up by the cells. It is not integrated into the chromosome but is independently transcribed and translated.

Chemical and physical vectors avoid the safety concerns associated with the use of biological vectors. The methods of use in the practice of this invention include, but are not limited to: liposomes, lipids, and amphiphiles, cell receptors, calcium phosphate or DEAE-dextran mediated transfection, microinjection, electroporation, and polypeptide-DNA complexes.

Liposomes are hollow, spherical carriers composed of phospholipids. When injected systemically, liposomes fuse with cell membranes or are taken into cells in the liver, spleen, lung, and reticuloendothelial system. To increase the target specificity, monoclonal antibodies or ligands directed to specific cell receptors have been attached to the surface of the liposome.

DNA within the liposomes is protected from degradation. In addition, the use of liposomes overcomes problems with cell barrier restrictions. Liposomes have the advantage of being biologically inert and do not pose the risk of replication as do viruses.

Cell receptor-targeted gene delivery is an alternative method. All cells contain general and unique receptors on their surface which bind to a number of agents or ligands. Ligands which bind to the receptor are often taken up and become part of the signal transduction pathway for gene activation. By targeting a unique receptor, a gene bound to ligands is taken up by specific cells without the concern of undesired cell types or overcoming cell surface resistance to enter the cell.

Calcium phosphate- or DEAE-dextran-mediated transfection is a widely used method of transfection. The transfected DNA enters the cytoplasm of the cell by endocytosis. Depending on the cell type, up to 20% of a population of cultured cells can be transfected at any one time.

The uptake of DNA by cells in culture is markedly enhanced when the nucleic acid is presented as a calcium phosphate-DNA coprecipitate. Graham and van der Eb (1973), who developed the procedure for the introduction of adenovirus and SV40 DNA into adherent cells, described the concentrations of calcium (125 mM) and DNA (5–30 $\mu$g/ml) that were optimal for formation of calcium phosphate-DNA coprecipitates at neutral pH (7.05). In addition, they established the optimal times for the precipitation reaction (20–30 minutes) and for the subsequent exposure of cells to the precipitate (5–24 hours). Their work laid the foundation for the introduction of cloned DNA into many different kinds of mammalian cells and led directly to reliable methods for stable transformation of cells and for transient expression of cloned DNAs. Many minor modifications of the procedure have been described, mostly involving permutations of the order and manner of mixing of ingredients in the precipitation reaction. Increases in the efficiency of the procedure have been achieved by incorporating additional steps such as glycerol shock and/or chloroquine treatment following the transfection protocol. Treatment with sodium butyrate has also been shown to enhance the expression in simian and human cells of plasmids that contain the SV40 enhancer.

DEAE-dextran was originally used as a facilitator to introduce poliovirus RNA and Sv40 and polyomavirus DNAs into cells. The procedure, with slight modifications, continues to be widely used for transfection of viral genomes and plasmids carrying viral sequences. Although the mechanism of action of DEAE-dextran is not known, it is thought that the polymer might bind to DNA and inhibit the action of nucleases and/or bind to cells and promote endocytosis of the DNA.

Transfection mediated by DEAE-dextran differs from calcium phosphate coprecipitation in three important respects. First, it is generally used only for transient expression of cloned genes and not for stable transformation of cells. Second, it works very efficiently with lines of cells such as BSC-1, CV-1, and COS but is unsatisfactory with many other types of cells, perhaps because the polymer is toxic. Third, smaller amounts of DNA are used for transfection with DEAE-dextran than with calcium phosphate coprecipitation. Maximal transfection efficiency of $10^5$ simian cells is achieved with 100–200 ng of supercoiled plasmid DNA; larger amounts of DNA (<2–3 $\mu$g) can be inhibitory. In contrast to transfection mediated by calcium phosphate, where high concentrations of DNA are required to promote the formation of a precipitate, carrier DNA is never used with the DEAE-dextran transfection method.

Many variants of DEAE-dextran transfection have been described. There are two important variables that greatly affect the efficiency of the method: the concentration of DEAE-dextran that is used and the length of time that the cells are exposed to the DNA/DEAE-dextran mixture. It is possible to use either a relatively high concentration of DEAE-dextran (1 mg/ml) for short periods (30 minutes to 1.5 hours) or a lower concentration (250 $\mu$g/ml) for longer periods of time (up to 8 hours). The first of these transfection procedures is the more efficient, but it involves monitoring the cells for early signs of distress when they are exposed to the facilitator. The second technique is less stringent and is therefore more reliable.

The polycation Polybrene™ allows the efficient and stable introduction of low-molecular-weight DNAs (e.g., plasmid DNAs) into cell lines that are relatively resistant to transfection by other methods.

Polybrene has been used as a facilitator of DNA transfection into cells that have proved to be relatively resistant to transfection using calcium phosphate coprecipitation. The method works efficiently for stable transformation of CHO cells by plasmid DNA, yielding approximately 15-fold more transformants than calcium phosphate-DNA coprecipitation. However, there is no difference between the two methods in the efficiency of transformation of high-molecular-weight DNA. It is not known whether Polybrene-mediated transfection can be used for transient expression of cloned DNA or whether it can be adapted for stable transformation with cell lines other than CHO.

Protoplast fusion is an alternative method of introducing the cDNA of this invention into the targeted cells. In this method, protoplasts derived from bacteria carrying high numbers of copies of a plasmid of interest are mixed directly with cultured mammalian cells. After fusion of the cell membranes (usually with polyethylene glycol), the contents of the bacteria are delivered into the cytoplasm of the mammalian cells and the plasmid DNA is transferred to the nucleus. Protoplast fusion is not as efficient as transfection for many of the cell lines that are commonly used for transient expression assays, but it is useful for cell lines in which endocytosis of DNA occurs inefficiently. Protoplast fusion frequently yields multiple copies of the plasmid DNA tandemly integrated into the host chromosome.

Cloned DNA can be introduced into mammalian cells by fusing protoplasts, prepared from bacteria carrying the plasmid DNA of interest, with cultured cells. The bacteria are grown in the presence of chloramphenicol to amplify the plasmid DNA and then treated with lysozyme to remove the cell wall. The resulting protoplasts are centrifuged onto a monolayer of mammalian cells, and the resulting mixture is treated with polyethylene glycol (PEG) to promote fusion. During this process, bacterial and plasmid DNAs are transferred into the mammalian call. PEG is then removed, and the cells are incubated in fresh tissue culture medium containing kanamycin to inhibit the growth of any surviving bacteria. Protoplast fusion has been used both for transient expression of cloned genes and for establishment of stable lines of mammalian cells.

Protoplast fusion has been used to stably introduce immunoglobulin genes into B cells and globin genes into mouse erythroleukemia cells. The advantage of this method is its high efficiency. However, the manipulations are time-consuming and cotransformation is usually not possible. Thus, the gene of interest must always be carried on a plasmid containing the desired selectable marker.

Electroporation involves the application of brief, high-voltage electric pulses to mammalian cells leading to the formation of nanometersized pores in the plasma membrane. DNA is taken directly into the cell cytoplasm either through these pores or as a consequence of the redistribution of membrane components that accompanies closure of the pores. Electroporation can be extremely efficient and can be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

The procedure has been used for both transient expression and stable transformation, but the efficiency of transfection has varied widely. It is essential to carry out a series of preliminary experiments to determine the conditions that lead to acceptable levels of transient expression or stable transformation for a particular cell line.

The efficiency of transfection by electroporation is influenced by a number of factors. 1) The strength of the applied electric field. At low voltage, the plasma membranes of cultured cells are not sufficiently altered to allow passage of DNA molecules; at higher voltage, the cells are irreversibly damaged. For most lines of mammalian cells, the maximal level of transient expression (as measured by assays of CAT activity, for example) is reached when voltages between 250 V/cm and 750 V/cm are applied. Typically, between 20% and 50% of the cells survive this treatment. 2) The length of the electric pulse. Usually, a single electric pulse is passed through the cells. Some electroporation devices allow the experimenter to control the length and shape of the pulse; in others, the characteristics of the pulse are determined solely by the capacitance of the power supply. The available data, indicate that the optimal length of the electric pulse required for electroporation is 20–100 milliseconds. The efficiency of transient expression is increased if the cells are incubated for 1–2 minutes in the electroporation chamber after exposure to the electric pulse. 3) Temperature. Some workers report that maximal levels of transient expression are obtained when the cells are maintained at room temperature during electroporation; others have obtained better results when the cells are maintained at 0° C. These discrepancies may result from differences in the responses of various types of mammalian cells to the passage of electric current or in the amount of heat generated during electroporation when large electrical voltages (>1000 V/cm) and/or extended electric pulses (>100 milliseconds) are used. 4) Conformation and concentration of DNA. Although both linear and circular DNAs can be transfected by electroporation, higher levels of both transient expression and stable transformation are obtained when linear DNA is used. Effective transfection has been obtained with concentrations of DNA ranging from 1 μg/ml to 40 μg/ml. 5) Ionic composition of the medium. The efficiency of transfection is many fold higher when the cells are suspended in buffered salt solutions (e.g., HEPES-buffered saline) rather than in buffered solutions of nonionic substances such as mannitol or sucrose. Electroporation has one major advantage: It works well with cell lines that are refractive to other techniques, such as calcium phosphate-DNA coprecipitation. However, considerable work may be required to define optimal conditions for the particular cell line under study. A number of different electroporation instruments are commercially available, and the manufacturers provide detailed protocols for their use.

Another important method for introducing DNA into cells is to couple the DNA to chemically modified proteins. These modified proteins have the ability to bind DNA through a chemically attached synthetic polylysine peptide, and bind to specific receptors on target cells. After these complexes are taken up by a specific receptor mediated endocytosis, the genes encoded by the DNA can be expressed by the target cell. Experiments have been performed with transferrin/polylysine/DNA complexes as well as with asialoglycoprotein/polylysine/DNA complexes. The covalently, chemically combined natural ligands are used: (1) to specifically target DNA to different tissues; (2) to provide more efficient uptake process. These methods are limited because they require in vitro modification of the ligands using chemical or enzymatic methods in order to create a compound capable of binding DNA. Alternatively, the DNA-binding protein technology of Ledley et al., as described in WO94/25608, may be used.

Liposomes have been intensively studied for their usefulness as delivery vehicles in vitro and in vivo. Most of these procedures involve encapsulation of DNA or RNA within liposomes, followed by fusion of the liposomes with the cell membrane. However, Eppstein, Felgner et al. have disclosed a method-of transfection in which DNA is complexed with a synthetic cationic lipid or amphiphile and introduced into cells by fusion.

A preferred method of administering a nucleic acid encoding for an IκB mutein of this invention is via transfection using a non-viral vector, preferably a cationic amphiphile (e.g. DOTMA) as described in U.S. Pat. No. 4,897,355, WO 95/14381, WO 96/18372, WO 96/01840, WO 96/01841, Proc. Nat. Acad. Sci.(USA), 93, 3176–3181 (1996) and U.S. provisional patent application, "Cationic Lipids for Gene Therapy," Paula N. Belloni et al., filed Oct. 22, 1996, the disclosures of which are incorporated by reference herein. This DNA transfection method can be used as part of a therapeutic protocol to treat inflammatory disorders. The treatment can be performed by either withdrawing cells from the affected patient, transfecting in vitro with the appropriate gene and reinjecting the successfully transfected cells; or by systemically administering the appropriate DNA directly into the affected patient with a suitable vehicle that will allow the transfection event to occur in vivo. The in vitro protocol is performed in the following way adapted from the literature (Anderson W F, Science 226, 401–409 (1984); Williams D A, Orkin S H, Mulligan RC, Proc. Nat. Acad. Sci. 83, 2655–2570 (1986)). A suitable quantity of tissue cells (from 10 million to 10 billion) is extracted from the patient. The tissue cells can be derived from various organs such as liver, spleen, blood or skin but most probably form bone marrow. The cells are prepared for tissue culture by trypsinization of the tissue or other means if necessary, grown in an appropriate media for a suitable length of time (e.g., 1 day to 2 weeks) and then transfected by adding the DNA/DOTMA liposome complex that is appropriate for the particular genetic disorder treated and with a composition consistent with the method described in the preceding. The cells are incubated for a suitable length of time, approximately 4 to 72 hours, and the successfully transfected cells are washed and reinjected back into the affected individual.

The in vivo transfection protocol can be performed following Nicolau et al., Proc. Nat. Acad. Sci. 80, 1068–1072 (1983). DNA liposome complexes, or double coated DNA complexes, or covalently modified double coated complexes are prepared as described by Eppstein et al. (supra). The covalently modified complexes may contain attached antibodies, proteins, hormones, carbohydrates or other chemical modifications so as to target them to the particular cells of interest. For instance, the complexes can contain an antibody to endothelial cells in order to target the complexes to the endothelial cells; or they can contain antibody to a particular subpopulation of bone marrow cells in order to target the complexes to those cells. The administration to the affected individual can be intravenous (IV), subcutaneous (SC), intraperitoneal (IP), intramuscular (IM), topical, or by aerosol to the nose or lung. The therapeutic protocol can involve either a single treatment or the complex can be given as often as required. The IV dose can be given as a bolus or by slow infusion.

The following examples are given to enable those skilled in the art to more clearly understand and to practice the present invention. They should not be considered as limiting the scope of the invention, but merely as being illustrative and representative thereof.

EXAMPLE 1

Construction of IκB Plasmids

The cDNA encoding human full length IκB (amino acids 1–317) was isolated from a human umbilical vein endothelial cell cDNA library (#937223, Strategene, La Jolla, Calif.) by PCR amplification. PCR amplification was performed according to the manufacturer's (GeneAmp kit, Perkin Elmer, Norwalk, Conn.) conditions using the following oligonucleotide primers (restriction endonuclease sites underlined):

Forward 5' ccgcgtctagacagctcgtccgcgccatgttcc 3' (SEQ ID NO:3)

Reverse 5' ccgccgaattcatacaagtccatgttctttcagcc 3' (SEQ ID NO:4)

Each of thirty amplification cycles was performed at 94° C. for 1 min (denaturation), 55° C. for 1.5 min (annealing), and 72° C. for 2 minutes (extension). This cDNA was ligated into a eukaryotic expression plasmid (pBJneo, Lin et al., Science 249:677–679 (1990)) after digestion with restriction endonucleases EcoRI and Xbal to produce the plasmid pIκB-fl. The IκB-NT truncation mutant (encoding amino acids 45–317) was constructed by PCR amplification using the plasmid encoding full length human IκB as template. PCR reactions were performed (as described above) using the following oligonucleotide primers (restriction endonuclease sites underlined):

Forward 5' ggctctagaatggtcaaggagctgcaggag 3' (SEQ ID NO:5)

Reverse 5' ccgccgaattcatacaagtccatgttctttcagcc 3' (SEQ ID NO:6)

The 885 bp PCR amplicon was digested with XbaI and EcoRI restriction enzymes and subcloned into the pBJneo eukaryotic expression plasmid to produce plasmid pIκB-NT.

Similarly other truncation mutants of IκB, having deletions at the carboxy-terminus were prepared as described above for full length IκB. The same forward primer was used with the following reverse primers for PCR amplification:

| IκB Truncate | Primer | |
|---|---|---|
| IκB#1 1–289 | cgcgaattcatagctctcctcatcctcactctc | (SEQ ID NO:7) |
| IκB#2 1–280 | cgcgaattccagcatctgaaggttttctagtgtc | (SEQ ID NO:8) |
| IκB#3 1–266 | cgcgaattcctgtatccgggtgcttgggcggcc | (SEQ ID NO:9) |
| IκB#4 1–242 | cgcgaattcatcagccccacacttcaacaggag | (SEQ ID NO:10) |

EXAMPLE 2
Construction of Control and Marker Plasmids

The human collagenase B promoter region (nucleotides −670 to +7) was PCR amplified from human genomic DNA. The human genomic DNA was obtained from a human EBV transformed B cell line using a commercially available kit (k1615-20, Turbogen, Invitrogen). The human collagenase B promoter region contains an NF-κB recognition site. (See Sato et al., Oncogene 8:395 (1993). PCR amplification was performed according to the manufacturers instructions as described above using the following oligonucleotide primers:

5' gcgaagcttctagaggctgctactgtcccctttactg 3' (SEQ ID NO:11)

5' cgcgcatgcccctccttgacaggcaagtgctgctc 3' (SEQ ID NO:12)

The amplified DNA was digested with Hind3 and Sph1 restriction endonucleases and ligated into a plasmid encoding β-galactosidase (pSDK-LacZ, Logan et al., *Development* 119:905–916 (1993)), and is referred to as pGelB. Human, mouse, and mutated mouse 3X NF-κB/lacZ plasmids (pNF-κB/LacZ) were prepared by ligation of the following oligonucleotides into the HindIII and SalI sites of plasmid pSDKLacZ-TK, which contains the minimal thymidine kinase promoter directing expression of the lacZ reporter gene:

Human 3X NF-κB:

5' agc TTG GGG ATT TCC GAT CGG GAC TTT CCG ATC GGG GAT TTC CGA C CCC TAA AGG CTA GCC CCT AAA GGC TAG CCC CTA AAG GCA GCT 3' (SEQ ID NO:13)

Murine 3x NF-κB:

5' AGC TTG GGA CTT TCC GAT CGG GAC TTT CCG ATC GGG ACT TTC CGAC CCT GAA AGG CTA GCC CTG AAA GGC TAG CCC TGA AAG GCA GCT 3' (SEQ ID NO:14)

Mutant mouse 3x NF-κB:

5' AGC TTC TCA CTT TCC GAT CCT CAC TTT CCG ATC CTC ACT TTC CGAG AGT GAA AGG CTA GGA GTG AAA GGC TAG GAG TGA AAG GCA GCT 3' (SEQ ID NO:15)

NF-κB recognition elements are underlined. The orientation of the inserted sequences was confirmed by DNA sequence analysis.

EXAMPLE 3
Method of Transfection and Assay

U20S cells (osteosarcoma cell line, ATCC Accession No. HTB96) were cultured in McCoy's 5A medium (Gibco/BRL Gaithersburg M.) containing 10% fetal bovine serum and penicillin/streptomycin at 37° C. 5% $CO_2$ incubators. Cells were harvested in log phase of growth (70% confluency) by treatment with PBS containing 2 mM EDTA. After centrifugation and washing, the cells were resuspended in PBS buffer containing Hepes (1.3 g/100 ml) pH7.0 and 50 ug/ml plasmid with $10^7$ cells/ml. The cell suspension was incubated at 4° C. for 30 minutes, and then electroporated at room temperature with a BioRad (Hercules, Calif.) electroporator at 250 mV, 960 uF settings. The cells were then diluted by addition of 6 ml of tissue culture medium and cultured in Costar microwells. The culture medium was changed after 20 hours. Ten hours before stimulation, the medium was replaced with OptiMEM (Gibco/BRL) medium. 18 hours prior to assay, phorbol 12-myristate 13-αcetate (PMA) was added to the microwells to a final concentration of 25 ng/ml.

After washing with cold PBS medium, the cells were harvested by scraping into 0.25 ml of PBS. After washing, the cells were resuspended in 60 ul of a solution containing 0.25M sucrose, 10 mM Tris HCl pH 7.4, 10 mm EDTA. Cell were lysed by three cycles of freezing using a dry ice/ethanol bath and thawing at 37° C. After centrifugation to remove nuclei and debris, the supernatant was removed for assay. The amount of protein in the cell lysate was determined using the Pierce (Rockford Ill.) protein assay kit according to the manufacturer's instructions. β-galactosidase activity in the cell lysate was measured using 4-methyl umbeliferyl β-D galactoside (MUG, Sigma #M1633) as substrate. Assays were performed in 96 well plates according to the manufacturers instructions. The amount of substrate hydrolyzed after incubation with cell lysate containing 5 ug of protein (1 to 10 ul) was measured fluorometrically using a CytoFluorII fluorometer (Millipore, Bedford, Mass.).

EXAMPLE 4
Inhibition of NF-κB Activation

This Example demonstrates that IκB-NT inhibits NF-κB activation in U20S cells. Cells were co-transfected, following Example 3, with plasmids encoding full length or truncated forms of IκB-α (pIκB-fl and pIκB-NT of Example 1) and plasmids having the LacZ reporter sequence and the human NF-κB recognition site (pNF-κB/LacZ of Example 2). The amount of NF-κB driven LacZ activity was measured in unstimulated and PMA-stimulated cells. As controls, cells were co-transfected with pGelB, the mutated NfκB recognition site plasmid (Example 2), or pCMV-LacZ (non-responsive to IκB), rather than pNF-κB/Lacz. The amount of β-galactosidase activity measured was normalized to the amount of protein in the cell lysate; results are presented in FIG. 2.

The pGelB cells can be seen to respond to PMA activation; both IκB-fl and Iκ-NT significantly reduce this response. Likewise the response of the cells denoted 3X NF-κB (pNF-κB/LacZ) is significantly attenuated by IκB-NT. The greater inhibition observed with IκB-NT versus IκB-fl is attributed to the resistance to degradation of the former. Absent a recognition site for NF-κB, there is no expression of LacZ and no β-gal activity. CMV-LacZ expression is known to be independent of IκB.

EXAMPLE 5

This Example demonstrates that the IκB muteins are resistant to activation induced proteolysis. The amount of full length and truncated IκB-α protein in U2OS cells 0, 5 or 15 minutes after activation was quantitated by immunoblotting with anti-IκB-α monoclonal antibodies. U2OS cells were transiently transfected with plasmids encoding full length and truncated forms of NFκB. Cell lysates were then prepared and proteins separated by gel electrophoresis on 15% polyacrylamide gels prior to immunoblotting.

Figure 3:
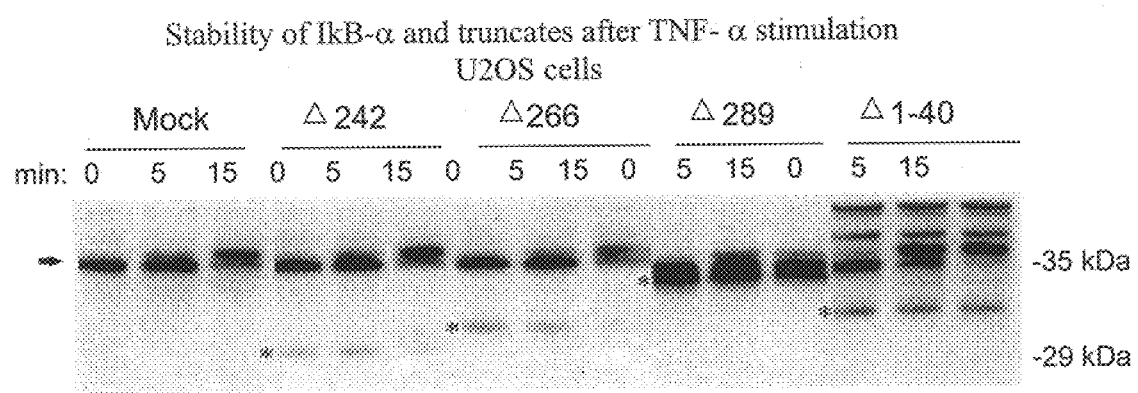
FIG. 3. IκB mutein resistance to activation induced proteolysis.

For each sample, $10^7$ U2OS were electroporated with 50 ug of plasmids of Example 1. They were cultured in Optimem medium after 36 hr. and after 72 hr were stimulated with 50 ng/ml TNF-α (Genzyme) for 0, 5, or 15 minutes. Cells were then lysed at 4° C. in lysis buffer containing 50 mM Hepes pH7.5, 150 mM NaCl, 10% glycerol, 1% Triton ×100, 1 mM EDTA, 1.5 mM $MgCl_2$, 100 mM NaF, and 10 mM Na pyrophosphate, 1 mM PMSF, 1 mM Na orthovanadate, 10 ug/ml aprotinin, 10 ug/ml leupeptin. Lysates were centrifuged to remove cell debris and nuclei, and 150 ug of protein was loaded onto each lane of a 15% SDS-PAGE gel. Immunoblotting was performed by the ECL method according to the manufacturer's instructions. Anti-IκBα/MAD-3 antibody (Santa Cruz Biotechnology #SD-203) was used as the primary antibody for full length and carboxy-truncated IκB-α and #SC-271 for IκB-NT. Results are shown in FIG. 3.

EXAMPLE 6

Figure 4:
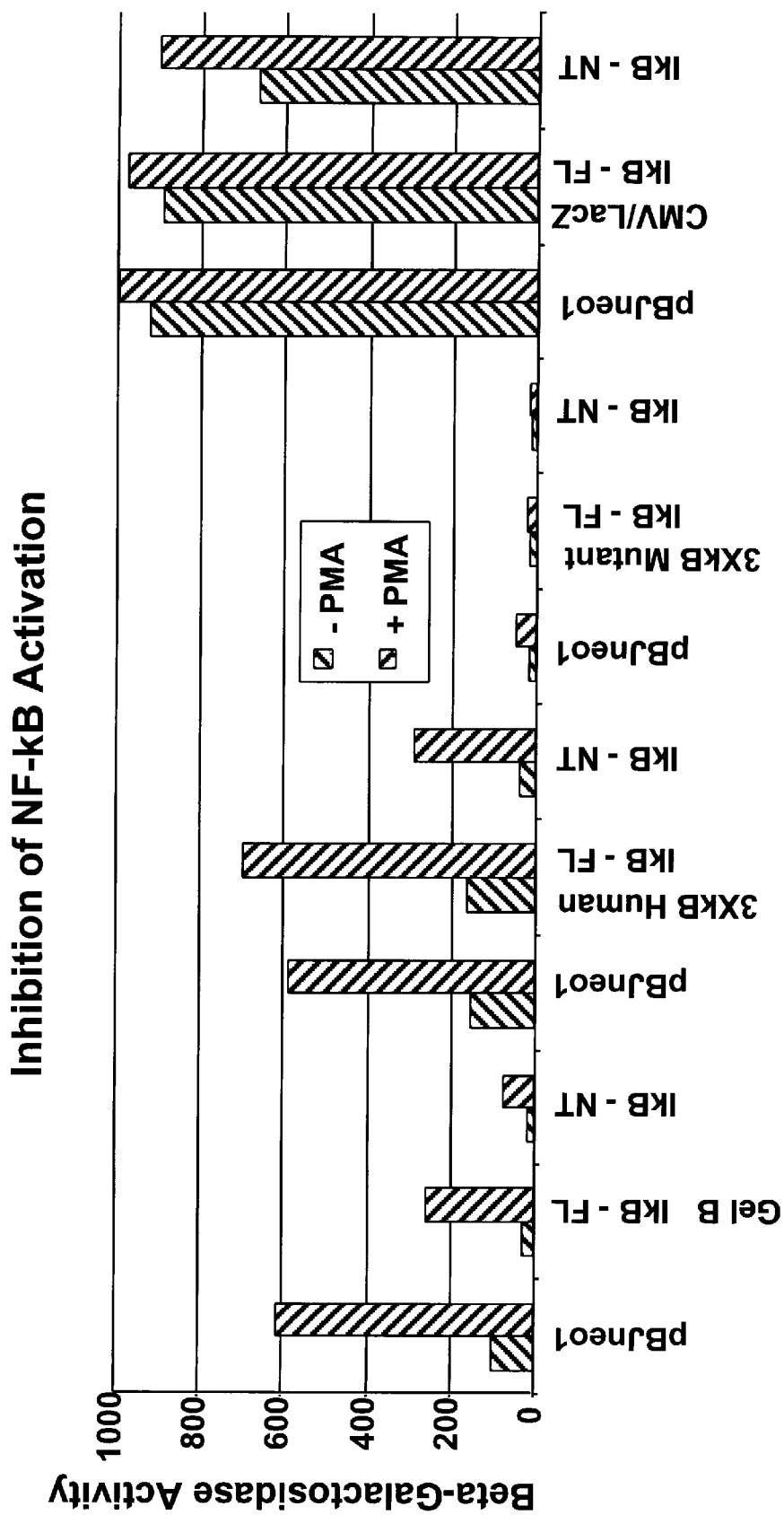
FIG. 4. IκB mutein inhibition of gelB promoter activity in a LacZ reporter gene cotransfection assay.

This Example demonstrates that the IκB truncates inhibit gelB promoter activity. U2OS cells were cotransfected with LacZ reporter gene plasmids (pGelB) and full length or truncated forms of IκB-α. The amount of β-galactosidase activity in unstimulated or PMA activated cells was then measured. All IκB truncates inhibit NF-κB activity, with IκB-NT being most active. Results are shown in FIG. 4.

EXAMPLE 7
Construction of Episomal Retroviral Vectors and Virus Production

Episomal retroviral expression vectors containing full length IκB (pWZRneo-IκB) or truncated IκB-NT (pWZRneo-IκB-NT) were constructed, following Kinsella and Nolan (Human Gene Therapy 7:1405:1413, 1996). The episomal vector was modified as follows: LZRA-LacZ(A) was cut with BspH1 generating a 7.5 kb fragment containing the EBV EBNA-1 and ori sequences. pWZLneo was cut with BspH1 to remove ampr sequences generating a 5.48 kb fragment. The 7.5 and 5.48 kb fragments were ligated to generate a hybrid EBV episomal retroviral vector containing neomycin resistance (pWZRneo).

Each vector was transfected into a high titre amphotrophic packaging cell line ø NX-A as described by Kinsella and Nolan generating three retroviral producer cell lines (ø-IκB/WT, ø-IκB/NT and ø-vector).

EXAMPLE 8
Retroviral-Based Expression of IκBα-Mutein in Human Endothelial Cells This Example demonstrates that IκB muteins expressed in human endothelial cells using a retroviral promoter are resistant to activation induced proteolysis. Human lung microvascular endothelial cells (HLMVEC) were purchased from Clonetics and cultured in DMEM/F12 media containing 5% fetal bovine serum and 10 ng/ml FGF at 370° C. in 6.5W $CO_2$ incubators. Iκb muteins were overexpressed in HLMVEC by retroviral transfection as follows. Retroviral culture supernatant was harvested from each producer cell line, and HLMVEC cultured in T-75 flasks were transduced with 10 ml of retroviral culture supernatant (ø-IκB/WT, ø-IκB/NT or ø-vector), supplemented with 12 ug/ml DEAE dextran+10 ng/ml FGF. The culture media was changed after 16 hours and cells were expanded in culture for 1 week post infection prior to analysis.

Figure 5:
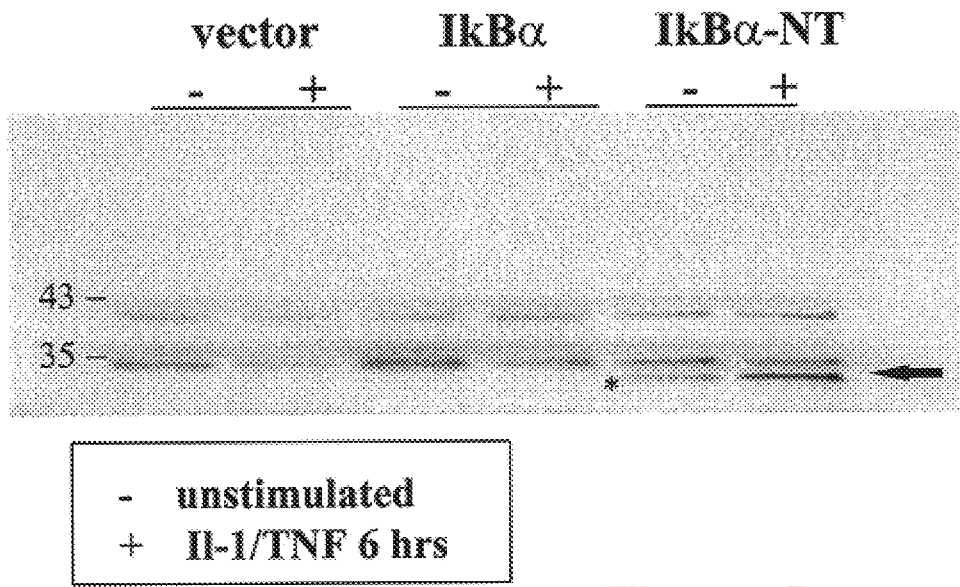
FIG. 5. Retroviral Based Expression in Human Endothelial Cells.

Expression of full length and truncated IκBα protein in transduced HLMVEC±activion was quantitated by immunoblotting. Transduced HLMVEC were cultured on T-75 flasks to confluence and incubated six hours with fresh media ±0.1 ng/ml of IL-1 and TNFα. Cell lysates and immunoblotting were prepared as described above in Example 5. Anti-IκBα IMAD-3 polycloanl antibody (Santa Cruz Biotechnology #SC-203) was used to detect full length IκB and SC-271 for IκB-NT. Results are shown in FIG. 5.

EXAMPLE 9
IκBαMutein Inhibits Expression of Inflammation Mediators in Vitro

Figure 6:
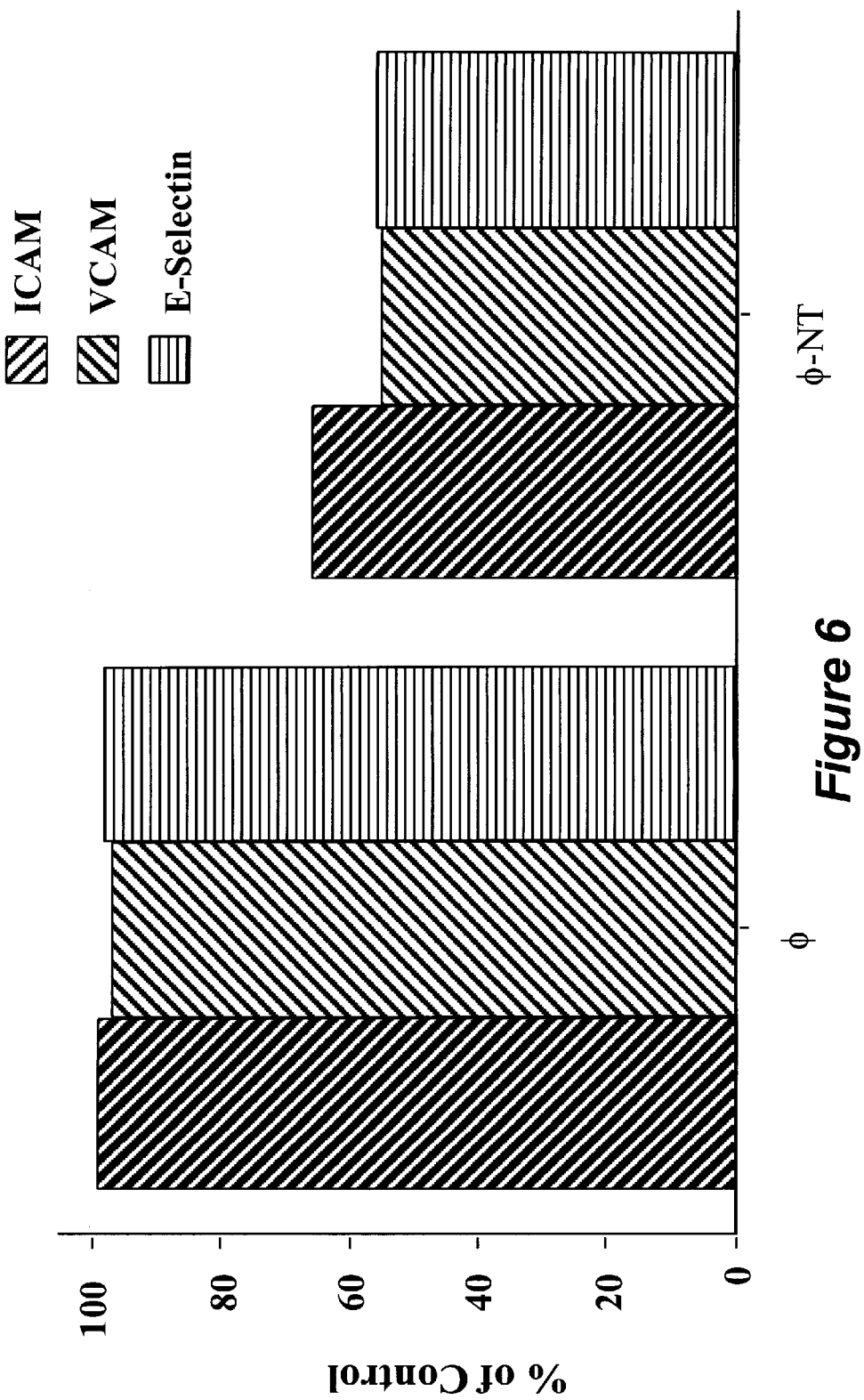
FIG. 6. Inhibition of Cytokine Induced CAM Expression.

This Example demonstrates that stable expression of IκB truncates inhibits the induction of cell adhesion molecules (ICAM, VCAM and e-selectin), as well as MCP-1 and IL-8 chemokines in cytokine-activated human lung microvascular endothelial cells (HLMVEC). ICAM, VCAM and e-selectin were quantitate by an ELISA using monoclonal antibodies (R&D Systems, α-ICAM BBA-3, α-VCAM BBA5, and α-ELAM BBA2) as follows. HLMVEC transduced with retroviral constructs containing neo-vector (ø-vector control), or N-terminal truncated IκB (ø-NT) were cultured in 96 well microtitre plates ±IL-1/TNF (0.1 ng/ml) for six hours. Cells were washed with PBS and fixed with 4% buffered formalin for 10 min, washed 3× with PBS containing 0.5% BSA (PBSB) and blocked with PBSB containing 10% normal goat serum. Monoclonal antibodies were added to triplicate wells at 0.1 ug/ml for 90 minutes followed by HRP-conjugated goat anti-mouse IgG for 30 min. Immunoreactivity was detected using IPD substrate and the change in OD detected spectometrically (Molecular Dynamics). Expression is presented as percent of the maximum response detected in cytokine stimulated HLMVEC ø-vector control cells. Results are shown in FIG. 6.

Figure 7:
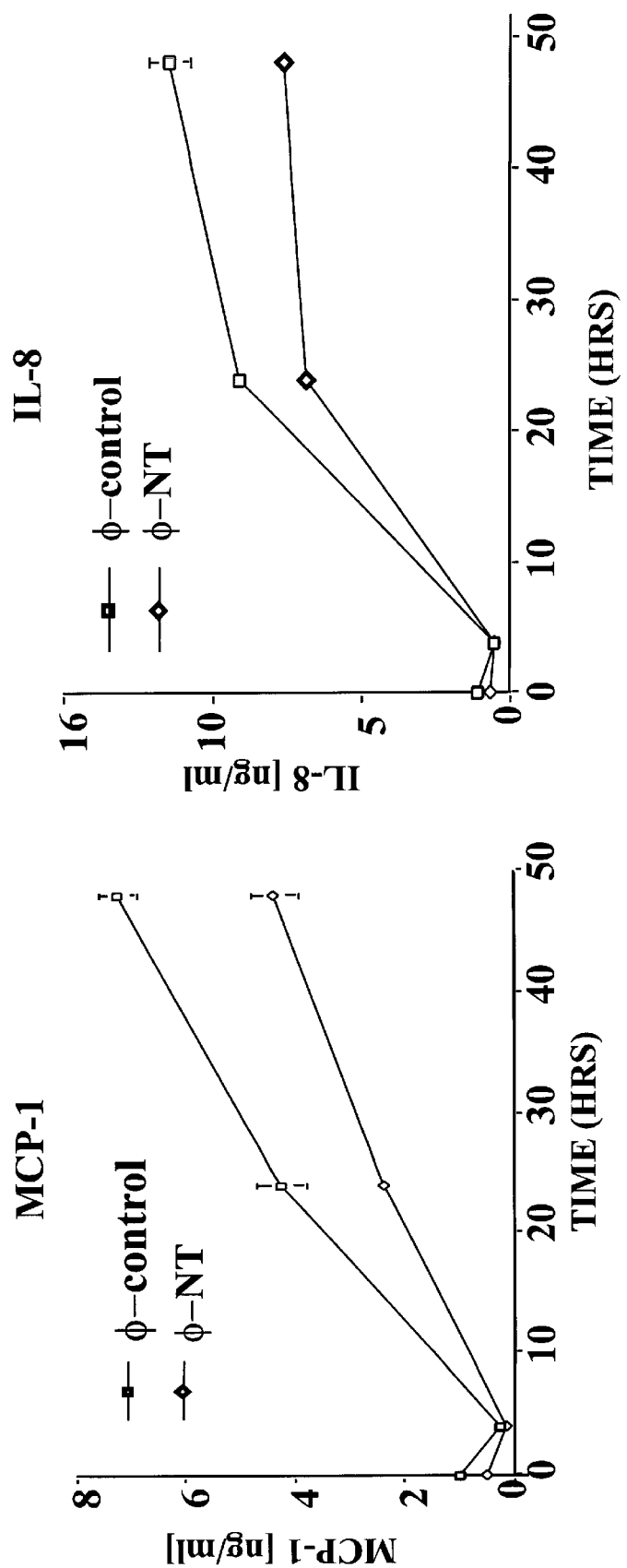
FIG. 7. Inhibition of Chemokine Production.

Expression and secretion of IL-8 and MCP-1 was measured in conditioned medium derived from HLMVEC/ø-vector or HLMVEC/ø-NT cells cultured in 24 well plates±IL-1/TNF (0.1ng/ml). Conditioned medium was harvested at 24 and 48 hours and MCP-1 and IL-8 levels were detected by ELISA (R&D Systems) exactly as described by manufacturer. Results are shown in FIG. 7.

EXAMPLE 10
IκB-NT Mutein Inhibits Inflammation in Vivo

Figure 8:
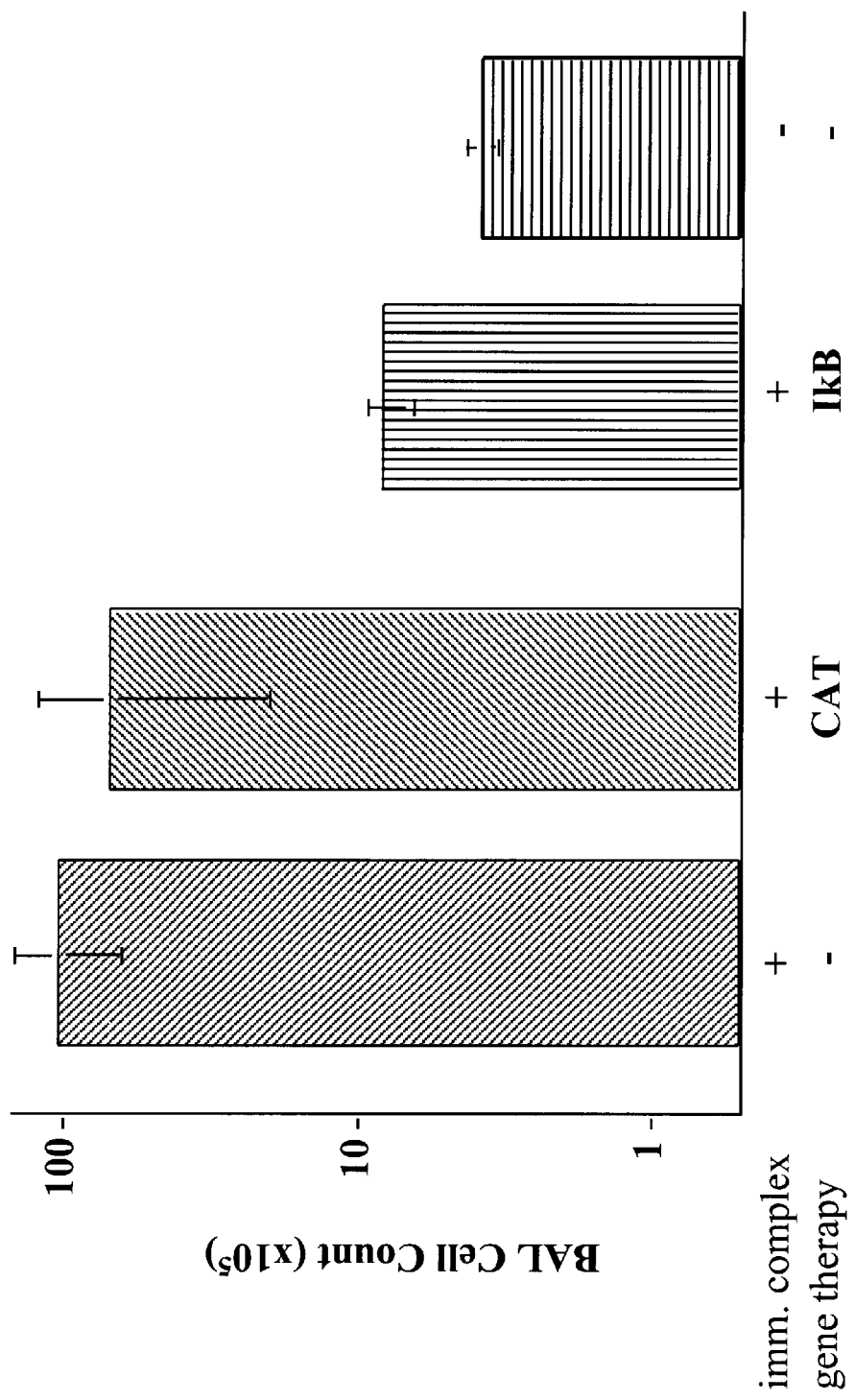
FIG. 8. Prophylatic In vivo Gene Therapy.

This Example demonstrates that topical application of IκB-NT inhibits immune-complex induced acute inflammation in rat lung. Plasmids containing a CMV promoter and bovine growth hormone polyadenylation sequences regulating the expression of IκBα-NT or a reporter gene chloramphenical acetyl transferase (CAT) were constructed. 100 ug of purified plasmid was instilled throughout the trachea into rat lungs using P10 tubing connected to a 30 gauge needle. Twenty-four hours post instillation of plasmid DNA, lung inflammation was induced by forming an IgG immune complex as described by Mulligan et al. (J. Clin. Invest; 88: 1396–1406). Briefly, 300 ul water containing 3 mg of rabbits BSA-IgG was instilled via the trachea of anesthetized rats followed immediately by an intravenous injection of 0.5 ml PBS containing 1 mg BSA (tail vein). Immune complex is formed within the lungs and acute inflammation was detected 4–24 hours later by measuring cellular influx into the bronchial lavage fluid (BAL) of the lungs. Upon animal sacrifice, the lungs were instilled with 10 ml of PBS to wash out cells in BAL, and cellular influx was quantitated by counting the total number of cells in 100 ul aliquots using a Coulter Cell Counter. Results from 24 hour time point are presented in FIG. 8, where it may be observed that the BAL cell count of the treated mice was an order of magnitude less than that of the controls.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed is:

1. An isolated nucleic acid encoding a protein, said protein mimicking the activity of IκB by inhibiting nuclear factor kappa B (NF-κB) mediated activation of the inflammatory response, said protein consisting of a sequence selected from the group consisting of amino acids 1–289 of SEQ ID NO:1, amino acids 1–280 of SEQ ID NO:1, amino acids 1–266 of SEQ ID NO:1, amino acids 1–242 of SEQ ID NO:1, and amino acids 45–317 of SEQ ID NO:1.

2. An expression vector comprising a nucleic acid of claim 1 operatively linked to regulatory elements necessary for expression of said nucleic acid.

3. A vector of claim 2 further comprising an inducible promoter.

4. An isolated nucleic acid consisting of SEQ ID NO:2.

5. An expression vector comprising a nucleic acid of claim 4 operatively linked to expression regulatory elements necessary for expression of said nucleic acid.

6. A vector of claim 5 further comprising an inducible promoter.

7. A plasmid comprising a cDNA consisting of the isolated nucleic acid of claim 1.

8. The plasmid of claim 7 which is pIκB-NT.

9. A complex between a cationic amphiphile and an expression vector comprising the isolated nucleic acid of claim 1.

10. A process for preparing a protein having IκB-like activity comprising:
    (a) transforming a host cell with an expression vector of claim 2;
    (b) culturing the host cell in a culture medium under conditions for amplification of the vector and expression of the protein; and
    (c) harvesting the protein from the culture medium.

* * * * *

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 317 amino acids
      (B) TYPE: amino acid
      (C) STRANDEDNESS:
      (D) TOPOLOGY: unknown (ii) MOLECULE TYPE: protein (iii) HYPOTHETICAL: NO (iv) ANTI-SENSE: NO (xi) SEQUENCE DESCRIPTION: SEQ ID NO:1:

```
Met Phe Gln Ala Ala Glu Arg Pro Gln Glu Trp Ala Met Glu Gly Pro
 1               5                  10                  15

Arg Asp Gly Leu Lys Lys Glu Arg Leu Leu Asp Asp Arg His Asp Ser
                20                  25                  30

Gly Leu Asp Ser Met Lys Asp Glu Glu Tyr Glu Gln Met Val Lys Glu
            35                  40                  45

Leu Gln Glu Ile Arg Leu Glu Pro Gln Glu Val Pro Arg Gly Ser Glu
        50                  55                  60

Pro Trp Lys Gln Gln Leu Thr Glu Asp Gly Asp Ser Phe Leu His Leu
65                  70                  75                  80

Ala Ile Ile His Glu Glu Lys Ala Leu Thr Met Glu Val Ile Arg Gln
                85                  90                  95

Val Lys Gly Asp Leu Ala Phe Leu Asn Phe Gln Asn Asn Leu Gln Gln
                100                 105                 110

Thr Pro Leu His Leu Ala Val Ile Thr Asn Gln Pro Glu Ile Ala Glu
            115                 120                 125

Ala Leu Leu Gly Ala Gly Cys Asp Pro Glu Leu Arg Asp Phe Arg Gly
        130                 135                 140

Asn Thr Pro Leu His Leu Ala Cys Glu Gln Gly Cys Leu Ala Ser Val
145                 150                 155                 160

Gly Val Leu Thr Gln Ser Cys Thr Thr Pro His Leu His Ser Ile Leu
```

|  |  | 165 |  |  |  | 170 |  |  |  | 175 |  |
|---|---|---|---|---|---|---|---|---|---|---|---|

Lys Ala Thr Asn Tyr Asn Gly His Thr Cys Leu His Leu Ala Ser Ile
            180             185          190

His Gly Tyr Leu Gly Ile Val Glu Leu Leu Val Ser Leu Gly Ala Asp
    195             200          205

Val Asn Ala Gln Glu Pro Cys Asn Gly Arg Thr Ala Leu His Leu Ala
210             215            220

Val Asp Leu Gln Asn Pro Asp Leu Val Ser Leu Leu Lys Cys Gly
225          230           235         240

Ala Asp Val Asn Arg Val Thr Tyr Gln Gly Tyr Ser Pro Tyr Gln Leu
         245          250         255

Thr Trp Gly Arg Pro Ser Thr Arg Ile Gln Gln Gln Leu Gly Gln Leu
    260             265          270

Thr Leu Glu Asn Leu Gln Met Leu Pro Glu Ser Glu Asp Glu Glu Ser
    275             280         285

Tyr Asp Thr Glu Ser Glu Phe Thr Glu Phe Thr Glu Asp Glu Leu Pro
  290             295          300

Tyr Asp Asp Cys Val Phe Gly Gly Gln Arg Leu Thr Leu
305          310           315

(2) INFORMATION FOR SEQ ID NO:2:

(i) SEQUENCE CHARACTERISTICS:
        (A) LENGTH: 819 base pairs
        (B) TYPE: nucleic acid
        (C) STRANDEDNESS: single
        (D) TOPOLOGY: unknown (ii) MOLECULE TYPE: cDNA (iii) HYPOTHETICAL: NO (iv) ANTI-SENSE: NO (xi) SEQUENCE DESCRIPTION: SEQ ID NO:2:

```
ATGGTCAAGG AGCTGCAGGA GATCCGCCTC GAGCCGCAGG AGGTGCCGCG CGGCTCGGAG      60

CCCTGGAAGC AGCAGCTCAC CGAGGACGGG GACTCGTTCC TGCACTTGGC CATCATCCAT     120

GAAGAAAAGG CACTGACCAT GGAAGTGATC CGCCAGGTGA AGGGAGACCT GGCCTTCCTC     180

AACTTCCAGA ACAACCTGCA GCAGACTCCA CTCCACTTGG CTGTGATCAC CAACCAGCCA     240

GAAATTGCTG AGGCACTTCT GGGAGCTGGC TGTGATCCTG AGCTCCGAGA CTTTCGAGGA     300

AATACCCCCC TACACCTTGC CTGTGAGCAG GGCTGCCTGG CCAGCGTGGG AGTCCTGACT     360

CAGTCCTGCA CCACCCCGCA CCTCCACTCC ATCCTGAAGG CTACCAACTA CAATGGCCAC     420

ACGTGTCTAC ACTTAGCCTC TATCCATGGC TACCTGGGCA TCGTGGAACT TTTGGTGTCC     480

TTGGGTGCTG ATGTCAATGC TCAGGAGCCC TGTAATGGCC GGACTGCCCT TCACCTCGCA     540

GTGGACCTGC AAAATCCTGA CCTGGTGTAC CTCCTGTTGA AGTGTGGGGC TGATGTCAAC     600

AGAGTTACCT ACCAGGGCTA TTCTCCCTAC CAGCTCACCT GGGGCCGCCC AAGCACCCGG     660

ATACAGCAGC AGCTGGGCCA GCTGACACTA GAAAACCTTC AGATGCTGCC AGAGAGTGAG     720

GATGAGGAGA GCTATGACAC AGAGTCGGAG TTCACGGAGT TCACAGAGGA CGAGCTGCCC     780

TATGATGACT GTGTGTTTGG AGGCCAGCGT CTGACGTTA                           819
```

(2) INFORMATION FOR SEQ ID NO:3:

(i) SEQUENCE CHARACTERISTICS:
        (A) LENGTH: 33 base pairs (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:3:

CCGCGTCTAG ACAGCTCGTC CGCGCCATGT TCC                           33

(2) INFORMATION FOR SEQ ID NO:4:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:4:

CCGCCGAATT CATACAAGTC CATGTTCTTT CAGCC                         35

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:5:

GGCTCTAGAA TGGTCAAGGA GCTGCAGGAG                               30

(2) INFORMATION FOR SEQ ID NO:6:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:6:

CCGCCGAATT CATACAAGTC CATGTTCTTT CAGCC                         35

(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:7:

CGCGAATTCA TAGCTCTCCT CATCCTCACT CTC                                    33

(2) INFORMATION FOR SEQ ID NO:8:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:8:

CGCGAATTCC AGCATCTGAA GGTTTTCTAG TGTC                                   34

(2) INFORMATION FOR SEQ ID NO:9:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:9:

CGCGAATTCC TGTATCCGGG TGCTTGGGCG GCC                                    33

(2) INFORMATION FOR SEQ ID NO:10:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:10:

CGCGAATTCA TCAGCCCCAC ACTTCAACAG GAG                                    33

(2) INFORMATION FOR SEQ ID NO:11:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:11:

GCGAAGCTTC TAGAGGCTGC TACTGTCCCC TTTACTG                                    37

(2) INFORMATION FOR SEQ ID NO:12:

(i) SEQUENCE CHARACTERISTICS:
       (A) LENGTH: 34 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:12:

CGCGCATGCC CTCCTTGACA GGCAAGTGCT GCTC                                       34

(2) INFORMATION FOR SEQ ID NO:13:

(i) SEQUENCE CHARACTERISTICS:
       (A) LENGTH: 88 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:13:

AGCTTGGGGA TTTCCGATCG GGACTTTCCG ATCGGGGATT TCCGACCCCT AAAGGCTAGC           60

CCCTAAAGGC TAGCCCCTAA AGGCAGCT                                              88

(2) INFORMATION FOR SEQ ID NO:14:

(i) SEQUENCE CHARACTERISTICS:
       (A) LENGTH: 88 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:14:

AGCTTGGGAC TTTCCGATCG GGACTTTCCG ATCGGGACTT TCCGACCCTG AAAGGCTAGC           60

CCTGAAAGGC TAGCCCTGAA AGGCAGCT                                              88

(2) INFORMATION FOR SEQ ID NO:15:

(i) SEQUENCE CHARACTERISTICS:
       (A) LENGTH: 88 base pairs
       (B) TYPE: nucleic acid
       (C) STRANDEDNESS: single
       (D) TOPOLOGY: linear (ii) MOLECULE TYPE: cDNA -continued

```
    (iii) HYPOTHETICAL: NO (iv) ANTI-SENSE: NO (xi) SEQUENCE DESCRIPTION: SEQ ID NO:15:

AGCTTCTCAC TTTCCGATCC TCACTTTCCG ATCCTCACTT TCCGAGAGTG AAAGGCTAGG        60

AGTGAAAGGC TAGGAGTGAA AGGCAGCT                                          88
```